(12) United States Patent
Lintz et al.

(10) Patent No.: US 10,646,137 B2
(45) Date of Patent: May 12, 2020

(54) SYSTEM FOR THREE-DIMENSIONAL MEASUREMENT OF FOOT ALIGNMENT

(71) Applicant: CurveBeam LLC, Warrington, PA (US)

(72) Inventors: Francois L. A. Lintz, Balma (FR); Guy D. C. Long, Surrey (GB); Ian G. Winson, Bristol (GB); Uwe Hans Mundry, Landrum, SC (US)

(73) Assignee: Curve Beam LLC, Hatfield, PA (US)

( * ) Notice: Subject to any disclaimer, the term of this patent is extended or adjusted under 35 U.S.C. 154(b) by 586 days.

(21) Appl. No.: 15/293,550

(22) Filed: Oct. 14, 2016

(65) Prior Publication Data

US 2017/0105658 A1    Apr. 20, 2017

Related U.S. Application Data

(60) Provisional application No. 62/241,513, filed on Oct. 14, 2015.

(51) Int. Cl.
*A61B 5/107* (2006.01)
*A61B 5/00* (2006.01)
(Continued)

(52) U.S. Cl.
CPC .......... *A61B 5/1074* (2013.01); *A61B 5/0064* (2013.01); *A61B 5/1079* (2013.01); *A61B 5/4595* (2013.01); *G06T 7/73* (2017.01); *A61B 6/032* (2013.01); *A61B 6/505* (2013.01); *A61B 2562/17* (2017.08); *A61B 2576/02* (2013.01); *G06T 2207/10081* (2013.01)

(58) Field of Classification Search
CPC ... A61B 5/1074; A61B 5/0064; A61B 5/1079; A61B 5/4595; G06T 7/73; G06T 2207/30004; G06T 15/08; G06F 19/321
See application file for complete search history.

(56) References Cited

U.S. PATENT DOCUMENTS

| | | | |
|---|---|---|---|
| 2005/0049816 A1 | 3/2005 | Oda et al. | |
| 2005/0122333 A1* | 6/2005 | Sumanaweera | G06T 15/005 345/502 |

(Continued)

OTHER PUBLICATIONS

Mikel L. Reilingh et al., "Measuring hindfoot alignment radiographically: the long axial view is more reliable than the hindfoot alignment view", Skeletal Radiology, vol. 39, No. 11, pp. 1103-1108 (2010).

(Continued)

*Primary Examiner* — Patrick Fernandes
(74) *Attorney, Agent, or Firm* — Faegre Drinker Biddle & Reath LLP

(57) ABSTRACT

A system for determining the alignment measurement of the foot and ankle is disclosed. The system uses data representative of a three dimensional scanned image of a patient's foot and ankle while the patient was applying weight on the foot. Next the system detects the three dimensional coordinates associated with at least three predetermined landmarks on the patent's foot in the scanned image. A ground plane is determined using the predetermined landmarks. A center of a talar dome is determined in the scanned data. An ankle offset lever arm id determined from the set of landmarks and center of the talar dome.

10 Claims, 3 Drawing Sheets

(51) Int. Cl.
*G06T 7/73* (2017.01)
*A61B 6/03* (2006.01)
*A61B 6/00* (2006.01)

(56) References Cited

U.S. PATENT DOCUMENTS

| | | |
|---|---|---|
| 2009/0227906 A1 | 9/2009 | Oster |
| 2014/0093153 A1 | 4/2014 | Sofka et al. |
| 2015/0208980 A1 | 7/2015 | Segal et al. |
| 2016/0262903 A1 | 9/2016 | West et al. |

OTHER PUBLICATIONS

Supplementary European Search Report dated Apr. 2, 2019 in corresponding EP Appl. No. 16856261.9.

International Search Report/Written Opinion (PCT/US2016/057009) dated Dec. 30, 2016.

Meric et al., "Tibial Slope is Highly Variable in Patients Undergoing Primary Total Knee Arthroplasty: Analysis of 13,546 Computed tomography Scans", The Journal of Arthroplasty, 30(7): 1228-1232 (2015).

Takeuchi et al., Biomechanics and Plantar Fasciitis: A Radiographic Study, Chapter 50, pp. 259-267 (2008).

Prasad et al., "Clinico-radiological assessment and their correlation in clubfeet treated with postero-medial soft-tissue release", International Orthopedic Journal, 33(1): 225-229 (2007).

Shalaby et al, "Correction of complex foot deformities using the V-osteotomy and the lizarov technique", Strategies Trauma Limb Reconslr. 2(1): Apr. 21-30, 2007 {Retrieved on Dec. 12, 2016] Retrieved from the Internet ,URL: http://www.paleyinstitute.org/medialfile/The%20correction%20of%20complex%20foot%20deformities%20using%20lizarov's%20dlstractlon%20osteotomies.pdf>.

Child et al., "The effect of hindfoot realignment in triple arthrodesis", J. Foot Ankle Surg. vol. 48, No. 3, pp. 285-293 (2009).

Fuchs et al., "Quality of life 20 years after arthrodesis of the ankle. A study of adjacent joints", J. Bone. Joint Surg. Br. vol. 85-B, No. 7, pp. 994-998 (2003).

Fukuda, et al., "Impact of talar component rotation on contact pressure after total ankle arthroplasty: a cadaveric study", Foot Ankle Int. vol. 31, No. 5, 404-411 (2010).

Guichet et al., "Effect of the foot on the mechanical alignment of the lower limbs", Clin. Orthop. Relat. Res., No. 415, pp. 193-201 (2003).

Haight et al., "Measuring standing hindfoot alignment: reliability of goniometric and visual measurements", Arch. Phys. Med. Rehabil. vol. 86, pp. 571-575 (2005).

Khan et al., "Effect of local alignment on compartmental patterns of knee osteoarthritis", J. Bone. Joint Surg. Am. vol. 90, No. 9, pp. 1961-1969 (2008).

Liau et al., "The effect of malalignment on stresses in polyethylene component of total knee prostheses—a finite clement analysis", Clin. Biomech. (Bristol, Avon) vol. 17, pp. 140-146 (2002).

Lintz et al., "Ground Reaction Force Calcaneal Offset: A new measurement of hindfoot alignment", Foot and Ankle Surgery: Official Journal of the European Society of Foot and Ankle Surgeons vol. 18, pp. 9-14 (2012).

Magerkurth et al., "Evaluation of hindfoot dimensions: a radiological study", Foot Ankle Int. vol. 27, No. 8, pp. 612-616 (2006).

Mendicino et al., "Long leg calcaneal axial and hindfoot alignment radiographic views for frontal plane assessment", J. Am. Podiatr. Med. Assoc. vol. 98, No. 1, pp. 75-78 (2008).

Saltzman et al., "The hindfoot alignment view", Foot Ankle Int. vol. 16, No. 9, pp. 572-576 (1995).

Stash et al., "Radiographic assessment of the hindfoot and ankle", Clin. Podiatr. Med. Surg. vol. 21, pp. 295-304 (2004).

Tuijthof et al., "Measuring alignment of the hindfoot", J. Biomech. Eng. vol. 126, No. 3, pp. 357-362 (2004).

Werner et al., "The effect of valgus/varus malalignment on load distribution in total knee replacements", J. Biomech. vol. 38, pp. 349-355 (2005).

Van Bergeyk et al., "CT analysis of hindfoot alignment in chronic lateral ankle instability", Foot Ankle Int. vol. 23, No. 1, pp. 37-42 (2002).

Viste et al., "Periprosthetic osteolysis after AES total ankle replacement: Conventional radiography versus CT-scan", Foot and Ankle Surgery: Official Journal of the European Society of Foot and Ankle Surgeons, vol. 21, pp. 164-170 (2015).

\* cited by examiner

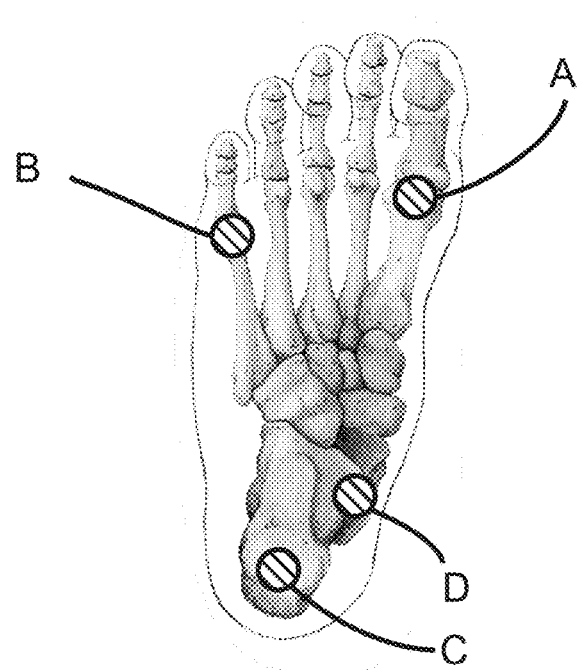
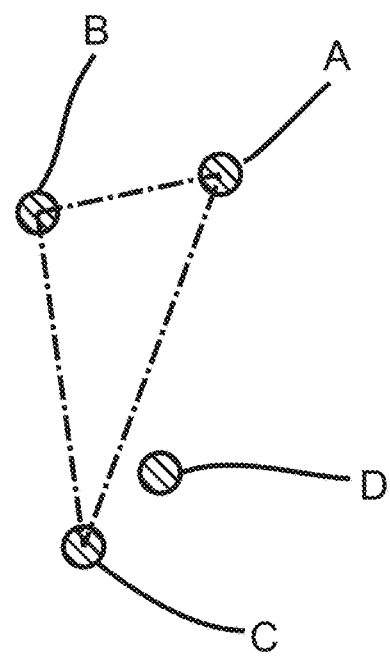
FIG. 2A
FIG. 2B
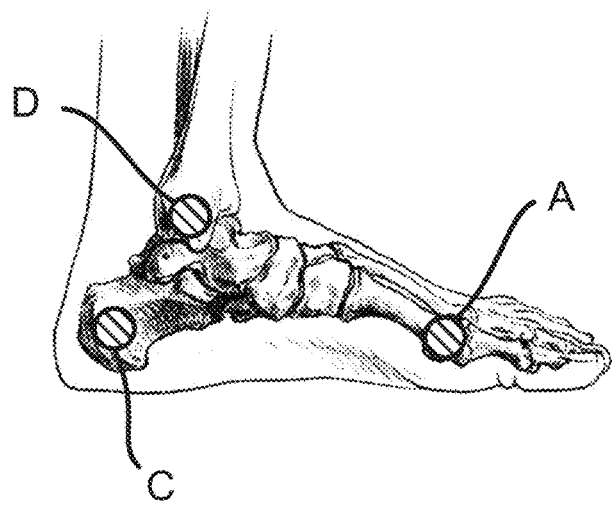
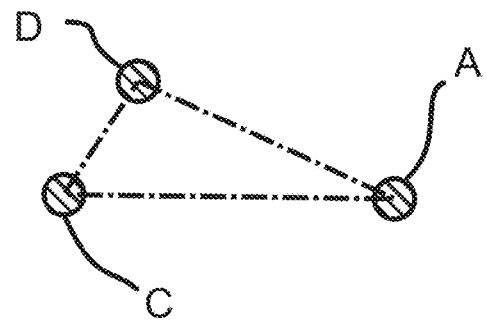
FIG. 3A
FIG. 3B

SYSTEM FOR THREE-DIMENSIONAL MEASUREMENT OF FOOT ALIGNMENT

RELATED APPLICATION

The present application is related to and claims priority from U.S. Provisional Patent Application No. 62/241,513, filed on Oct. 14, 2015, the disclosure of which is incorporated herein by reference in its entirety.

FIELD OF THE INVENTION

The present invention is directed to a system for measuring foot-ankle three-dimensional weight-bearing alignment using multi-dimension (e.g., 3D) weight bearing radiographic data.

BACKGROUND

Currently measurements of tibial-calcaneal or vertical-calcaneal alignment are performed using two-dimensional standard radiographs and applying various radiographic protocols, such as the long-leg view, Meary, Saltzman, or Cobey. See, for example, Mendicino, R. W., Catanzariti, A. R., John, S., Child, B. & Lamm, B. M., "*Long leg calcaneal axial and hindfoot alignment radiographic views for frontal plane assessment,*" J. Am. Podiatr. Med. Assoc. 98, 75-78 (2008); Saltzman, C. L. & el-Khoury, G. Y., "*The hindfoot alignment view,*" Foot Ankle Int. 16, 572-576 (1995); Strash, W. W. & Berardo, P., "*Radiographic assessment of the hindfoot and ankle,*" Clin. Podiatr. Med. Surg. 21, 295-304, v (2004); and Tuijthof, G. J., Herder, J. L., Scholten, P. E van Dijk, C. N. & Pistecky, P. V., "*Measuring alignment of the hindfoot,*" J. Biomech. Eng. 126, 357-362 (2004). Each of these methods uses two dimensional data obtained from radiographic scan and bases all the foot ankle alignment assessments off of those scans. In each case, the protocols do not take into account the relation of the forefoot with the hindfoot. Instead, they only provide a measurement of the hind-foot-ankle-leg alignment. As such, it is not a complete-foot-ankle alignment measurement.

The inventors have determined that the existing methods' failure to take into account the measurement of the forefoot results in less precision due to poorly reproducible radiographic protocols. Also, since the prior methods rely solely on hindfoot measurement, the accuracy of the overall measurement geometrically depends on the rotation of the lower limb.

A need therefore exists for an improved method for providing foot-ankle alignment measurement.

SUMMARY OF THE INVENTION

A system for determining alignment measurement of the foot and ankle, referred to as foot-ankle offset (FAO) based on utilization of three dimensional imaging and determination of a three dimensional foot alignment measurement referring to herein as the Torque Ankle Lever Arm System, (TALAS™). The system and related process uses medical imaging devices to obtain 3D coordinates for a set of anatomical landmarks and an algorithm generates a precise measure of human static ankle intrinsic lever arm for use in diagnostic and surgical planning processes.

In one embodiment, the system determines the alignment measurement of the foot and ankle using data representative of a three dimensional scanned image of a patient's foot and ankle while the patient was applying weight on the foot. The scanned data is correlated to determine the three dimensional location of the foot relative to the scanner in a predetermined coordinate system. Next the system detects the three dimensional coordinates associated with at least three predetermined landmarks on the patent's foot in the scanned image. A ground plane is determined using the predetermined landmarks. A center of a talar dome is determined in the scanned data. An ankle offset lever arm id determined from the set of landmarks and center of the talar dome.

The ground plane is preferably determined using center points of the landmarks. A triangular pyramid may be configured as representative of the patient's foot with the vertical apex being the center of the talar dome and the base being the ground plane.

The landmarks may include the first and fifth metatarsal bones in the foot and the greater tuberosity of the calcaneus. The image data may be analyzed using point detection to determine the approximate three-dimensional coordinates of the center of each landmark.

In an embodiment the system determines the center of each landmark by analyzing slices of the scanned data and determining the center of the tuberosity based on that analysis. Alternatively, a user may select the three dimensional center point of each landmark on a computer monitor depicting the scanned image.

The ground plane if preferably defined by a plane passing through the center points of the landmarks.

In an embodiment the ankle offset lever arm involves determining an ankle offset point on the ground plane that is an orthogonal projection from the ground plane to the center point of the talar dome, determining a forefoot center point on the ground plane that is the center between the center points of the landmarks for the first and fifth metatarsal bones, defining a line extending between the center point of the landmark of the greater tuberosity of the calcaneus to the forefoot center point, where the ankle offset lever arm is the length of an orthogonal projection on the ground plane from the line to the ankle offset point.

The torque on the ankle may be calculated by multiplying the weight of the patient times the length of the ankle offset lever arm.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

FIG. 2A is a top view of the bones in a foot with the locations of landmarks and talar dome shown.

FIG. 2B is a graphical depiction of the points in FIG. 2A.

FIG. 3A is a side view of the bones in a foot with the locations of landmarks and talar dome shown.

FIG. 3B is a graphical depiction of the points in FIG. 3A.

DESCRIPTION OF THE EMBODIMENTS

Figure 1:
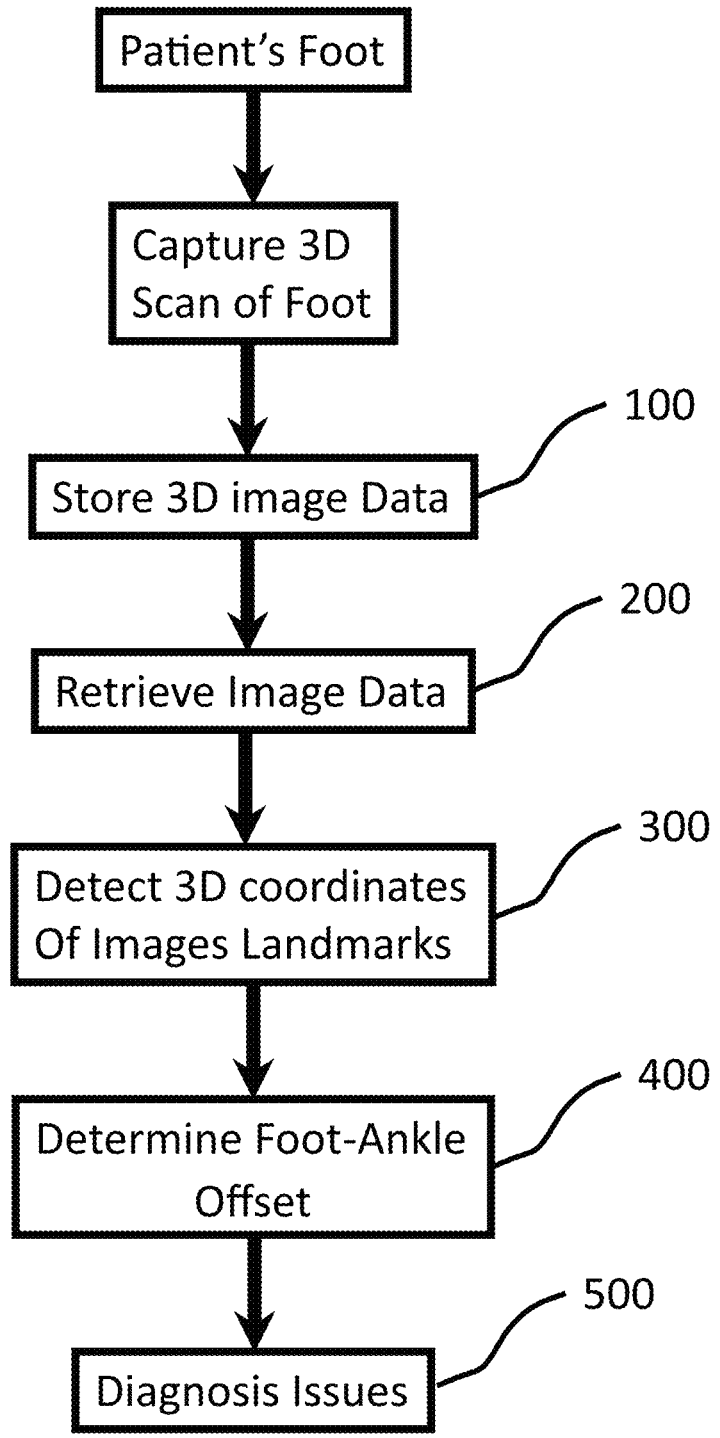
FIG. 1 is a flowchart depicting one embodiment of the steps involved in the process for determining foot-ankle offset.

Correct alignment is the main objective related to many orthopaedic surgical trauma and degenerative corrective procedures in the human body. It is well recognized that correct alignment improves joint pressure distribution, (see, for example, Fukuda, T., Haddad, S. L., Ren, Y. & Zhang, L. Q., "*Impact of talar component rotation on contact pressure after total ankle arthroplasty: a cadaveric study*," Foot Ankle Int. 31, 404-411 (2010); Liau, J. J., Cheng, C. K., Huang, C. H. & Lo, W. H., "*The effect of malalignment on stresses in polyethylene component of total knee prostheses*—a finite element analysis," Clin. Biomech. (Bristol, Avon) 17, 140-146 (2002); and Werner, F. W., Ayers, D. C., Maletsky, L. P. & Rullkoetter, P. J., "*The effect of valgus/varus malalignment on load distribution in total knee replacements*," J. Biomech. 38, 349-355 (2005)) and ligament tension and muscle function[14] (see, Van Bergeyk, A. B., Younger, A. & Carson, B., "*CT analysis of hindfoot alignment in chronic lateral ankle instability*," Foot Ankle Int. 23, 37-42 (2002).) In turn, this prevents early joint degeneration (arthrosis), which is a major public health issue, leading to pain and disability. (See, Khan, F. A. et al., "*Effect of local alignment on compartmental patterns of knee osteoarthritis*," J. Bone. Joint Surg. Am. 90, 1961-1969 (2008); and Werner, F. W., Ayers, D. C., Maletsky, L. P. & Rullkoetter, P. J., "*The effect of valgus/varus malalignment on load distribution in total knee replacements*," J. Biomech. 38, 349-355 (2005).)

In the native foot and ankle, disturbed alignment has proven to increase the rate of arthrosis, ankle instability. See, Child, B. J., Hix, J., Catanzariti, A. R., Mendicino, R. W. & Saltrick, K., "*The effect of hindfoot realignment in triple arthrodesis*," J. Foot Ankle Surg. 48, 285-293 (2009); Fuchs, S., Sandmann, C., Skwara, A. & Chylarecki, C., "*Quality of life 20 years after arthrodesis of the ankle. A study of adjacent joints*," J. Bone. Joint Surg. Br. 85, 994-998 (2003); Guichet, J. M., Javed, A., Russell, J. & Saleh, M., "*Effect of the foot on the mechanical alignment of the lower limbs*," Clin. Orthop. Relat. Res., 193-201 (2003); and Van Bergeyk, A. B., Younger, A. & Carson, B., "*CT analysis of hindfoot alignment in chronic lateral ankle instability*," Foot Ankle Int. 23, 37-42 (2002). In the operated foot and ankle, disturbed alignment increases total ankle replacement failure rates through aseptic loosening, and the rate of peripheral joints arthrosis in ankle arthrodesis.

In the case of ankle and hindfoot surgery, the only measurement used for planning surgery today is the angle between the leg or the vertical and the hindfoot (calcaneus bone) See, for example, Haight, H. J., Dahm, D. L., Smith, J. & Krause, D. A., "*Measuring standing hindfoot alignment: reliability of goniometric and visual measurements*," Arch. Phys. Med. Rehabil. 86, 571-575 (2005); Magerkurth, O., Knupp, M., Ledermann, H. & Hintermann, B., "*Evaluation of hindfoot dimensions: a radiological study*," Foot Ankle Int. 27, 612-616 (2006); Mendicino, R. W., Catanzariti, A. R., John, S., Child, B. & Lamm, B. M., "*Long leg calcaneal axial and hindfoot alignment radiographic views for frontal plane assessment*," J. Am. Podiatr. Med. Assoc. 98, 75-78 (2008); Saltzman, C. L. & el-Khoury, G. Y., "*The hindfoot alignment view,*" Foot Ankle Int. 16, 572-576 (1995); Strash, W. W. & Berardo, P., "*Radiographic assessment of the hindfoot and ankle*," Clin. Podiatr. Med. Surg. 21, 295-304, v (2004); and Tuijthof, G. J., Herder, J. L., Scholten, P. E., van Dijk, C. N. & Pistecky, P. V., "*Measuring alignment of the hindfoot*," J. Biomech. Eng. 126, 357-362 (2004). This angle is in itself flawed since there have been many different descriptions, all using different anatomical landmarks. Also, in many cases, measurements imply the use of external non-radiolucent markers, introducing another variable in the analysis, reducing precision and augmenting risk of error. Most important, depending on rotation of the limb, the value of hindfoot alignment varies considerably.

This implies that inevitably, a number of patients will either not be precisely assessed or not be corrected depending on measurement flaws. Of course, in a proportion of these cases, human medical intervention will be able, through experience, to counteract these effects. However, experience and literature show that in a number of cases, there are still surgical failures that are not explainable with current alignment measurements. See, Viste, A. et al., "*Periprosthetic osteolysis after AES total ankle replacement: Conventional radiography versus CT-scan*," Foot and Ankle Surgery: Official Journal of the European Society of Foot and Ankle Surgeons, 21, 164-170, doi:10.1016/j.fas.2014.11.002 (2015).

The inventors have previously published a study to alert the medical community on this matter. See, Lintz, F. et al., "*Ground Reaction Force Calcaneal Offset: A new measurement of hindfoot alignment*," Foot and Ankle Surgery: Official Journal of the European Society of Foot and Ankle Surgeons 18, 9-14, doi:10.1016/j.fas.2011.01.003 (2012). A primitive algorithm was devised which was based on the use of standard plain radiographs, taken at 90° angles. It enabled the inventors to validate the concept of the mechanical relationship between the hindfoot and forefoot and provide better results than the traditional measurement. However, the algorithm was only calculated in an "ideal", (theoretically) perfectly balanced foot and was still flawed when values diverged from this situation. Furthermore, since the required radiographic and data extraction protocol was complicated and time consuming, radiographers would have to be taught the protocol and, with so much manual human intervention involved, the reproducibility was questionable, and the whole process was not fit for daily clinical use.

The present invention provides a computer/software application which uses weight-bearing three dimension CT scan data to determine the foot-ankle offset. Specifically, one weight-bearing CT cone-beam scanner that is particularly useful in the present invention is the PedCAT® CT scanner sold by CurveBeam, LLC. However the present invention can also be used with standard radiographs, EOS imaging or other forms of weight bearing CT technology enabling image acquisition up to and above knee level, standard CT scanning machines with weight bearing simulation, and weight bearing MRI scanning machines. This tool is compatible for use with 4D imaging solutions that are currently being developed.

As mentioned above, the present invention measures the alignment of the foot using three dimensional weight-bearing data. Using that data, the foot ankle offset (FAO) is determined, replacing the old tibial-calcaneal angle. The following outlines the steps of the process that the system undertakes to achieve the FAO. However, this is not restrictive of the many measurements, called 3D-Biometrics, which will emerge from the use of the TALAS technology, based on the 3D measurement of offsets or angles between different landmarks in the foot and ankle.

Referring to the figures, the patient's foot is scanned (Step 100) using a weight-bearing CT scan and the raw data is stored. Step 200. The scan should be taken of the patient in neutral (normal standing) position. The program includes a mathematical algorithm to adjust the scanned data based on the positioning of the feet relative to the machine and each other in order to provide consistent data. The data is then analyzed to detect the 3D coordinates of specific anatomical landmarks in the foot. Step 300 Preferably those landmarks are the center of the first and fifth metatarsal bones heads (A and B, respectively) and the center of the greater tuberosity of the calcaneus (C), which are detected on the weight-bearing or ground plane. One method for determining this is to analyze slices of the scanned data until all three points (A, B, C) are detected in accordance with well-known techniques for point detection. That defines the ground plane. The center of the talar dome (D) is also detected. This is not restrictive of any future development of technology (such as automatic segmentation through clustering or machine learning) enabling a possibly more precise or more reproducible way to determine the landmarks. Also the acquisition of great quantities of data (big data) by this means, and the subsequent analysis of this data may result in selection of different or additional landmarks. Also, it is envisioned that the software can be modified to add more landmarks to the system so as to create a more complete analysis of the foot and ankle in order to encompass more conditions. For instance, landmarks can be added on each of the metatarsal bones to better analyze the structure of the forefoot.

Using these points, a triangular based pyramid is defined with the summit of the pyramid being the center of the talar dome (D). The system is preferably configured to automatically analyze the 3D data to determine these landmarks. However, it is also contemplated that the software could display the 3D data of the foot and ankle image on a computer screen and permit a physician or technician to manually select the landmark positions. The software may permit the user to rotate the image so as to allow for a more precise selection of the center point of the talar dome (D). Precise determination of these anatomical landmarks is important in order to obtain a high degree of intra and inter observer reproducibility. Future technological development and automation of the process will contribute to this.

The torque on the ankle is determined by the body weight (gravity) and ground reaction force acting on the ankle coronal plane through the talar dome. Since gravity is perpendicular to the ground plane, calculations are based on orthogonal projections of the talar dome on the ground plane. Using the 3D static model of the foot and the detected landmarks, the program calculates the anatomical offset or lever arm (D'F vector), which characterizes each patient's foot. Step 400. This is done by determining the orthogonal projection (D') of the center of the talus (D) on the ground plane (the plane upon which points A, B and C lie (FIG. 4) and which represent points on the ground upon which the patient's foot is standing). If desired, the ground plane can be adjusted to account for the offset from the true ground (bottom of the foot).

Figure 4:
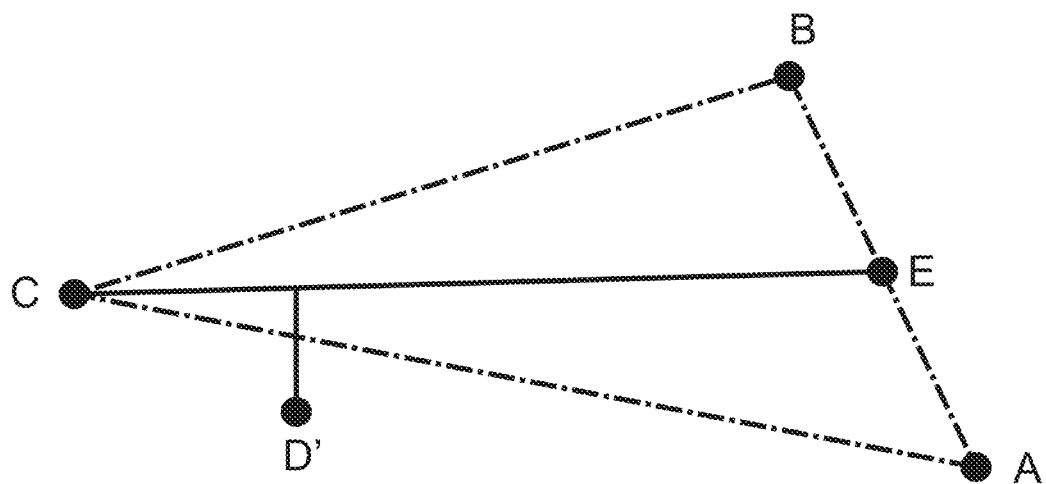
FIG. 4 is a graph depicting a measurement of the torque developed by body weight (gravity) and ground reaction force in the ankle coronal plane which includes a highest point on the talar dome.
Figure 5:
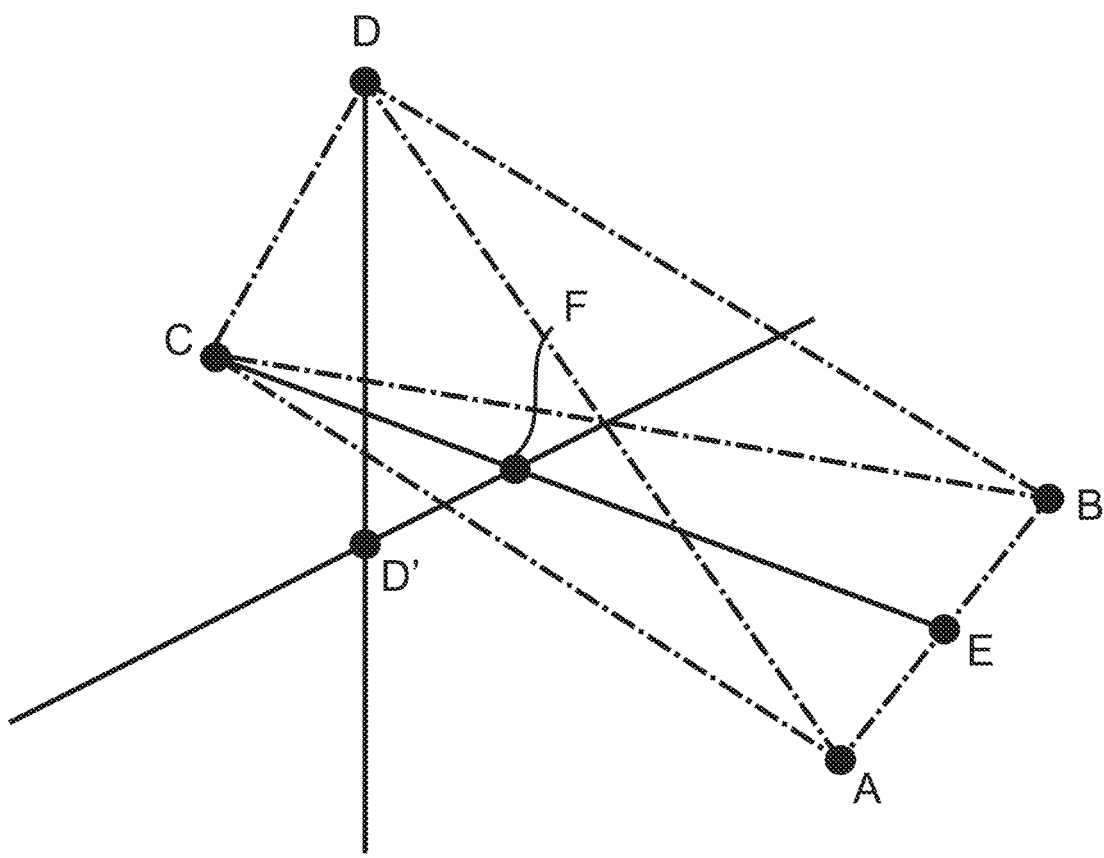
FIG. 5 is a three dimensional graphical model of the foot-ankle alignment measurement.

To determine point F, the system determines the midpoint (E) between points A and B, and then projects a line in the ground plane to point C. A line is then projected from point D' orthogonal to the line CE. Point F is located at the intersection of the line orthogonal to D' and line CE. FIG. 4.

As mentioned above, the vector D'F is the minimal ankle lever arm length and uniquely identifies a person's foot. To remove any pixel-size discrepancies, the length of the vector D'F is divided by the length of the line segment CE, which is representative of the overall foot length, and then multiplied by 100 to provide a percentage. This is the three dimensional foot ankle offset (3D FAO).

The present invention contemplates that, based on analysis of the feet of a significant portion of patients, a "normal" value of the offset can be determined. The 3D FAO of the person being analyzed can then be compared to the normal 3D FAO for determining potential foot/ankle issues. Step 500. A foot without any FAO issues should have a comparison to the "normal" that is close to zero or slightly negative. The system can visually depict on the patient's 3D FAO and the "normal" (which may include a Gaussian distribution around the "normal"). For example the patient's 3D FAO may be overlapped on top of the Gaussian distribution of the "normal", thus providing the physician and patient with a quick visual understanding of where the patient is relative to the norm. What is determined to be the "normal" may vary based on certain characteristics, including age or ethnicity.

The TALAS™ system can be used to not only detect preoperative issues, but can be used to provide a reliable means of simulating osteotomies and checking corrections post-operatively, or intra-operatively, should intra-operative 3D imaging and planning devices be available.

In one initial study using existing data, the inventors have been able to determine that the use of 3D data for measurement of foot-ankle alignment improves correlation coefficients between alignment values and real values from 0.78 to 0.93. The use of the TALAS™ system described above increased this coefficient from 0.93 to 0.99. Considering the number of foot and ankle alignment cases operated on each year in the world, the TALAS™ system may represent a health improvement for between 60 to 220 patients for every 1000 patients treated each year, either immediately or on a longer term, correlating with less time off work, less health costs, and less revision surgeries. Although the above discussion has explained the invention with respect to the analysis of the fore-foot, those skilled in the art would readily appreciate its applicability to mid-foot and hind-foot analysis also.

As discussed above, the TALAS™ procedure is preferably part of a software system which allows individual patient data, including the ankle offset calculation to be collected and stored for historical analysis, thus permitting tracking of a patient's development over time. Graphical depictions of the patient's development can be generated and displayed, providing a visual perception of the development.

The system or systems described herein may be implemented on any form of microprocessor. The system of the present invention may include a software program stored on the microprocessor and/or storage device (e.g., media). The method may be implemented through program code or program modules stored on a non-volatile computer-readable storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

The articles and publications referred to above are each incorporated herein by reference in their entirety.

The invention claimed is:

1. A method configured to be performed by a processor for determining an alignment measurement of foot and ankle bones of a patient while the patient is weight bearing, the method comprising the steps of:
   receiving scanned data in the processor representative of a three dimensional scanned image of the foot and ankle bones of the patient while the patient was applying weight on a foot;
   adjusting the scanned data to correlate a three dimensional location of the foot and ankle bones of the patient relative to a predetermined coordinate system;
   detecting three dimensional coordinates associated with at least three predetermined landmarks on the foot and ankle bones of the patient in the scanned data;
   receiving by the processor a selection by a user of a three dimensional center point of each landmark of the at least three predetermined landmarks on a computer monitor depicting the scanned data;
   wherein the at least three predetermined landmarks include a first metatarsal bone and a fifth metatarsal bone and a greater tuberosity of the calcaneus in the foot and ankle bones of the patient in the scanned data;
   determining a ground plane in the scanned data;
   determining a center of a talar dome in the scanned data based on a three dimensional shape of the talar dome, including a vertical and a horizontal location of the center of the talar dome relative to the ground plane; and
   determining an ankle offset lever arm from the at least three predetermined landmarks and the center of the talar dome.

2. The method according to claim 1, wherein the ground plane is determined using center points of the at least three predetermined landmarks.

3. The method according to claim 1, further comprising a step of defining a triangular pyramid with a vertical apex being the center of the talar dome and a base being the ground plane.

4. The method according to claim 1, data, and wherein the processor analyzes the scanned data using point detection to determine the approximate three-dimensional coordinates of a center of each landmark of the at least three predetermined landmarks.

5. The method according to claim 4, wherein the processor determines the center of each landmark by (i) analyzing slices of the scanned data and (ii) determining a center of a tuberosity of each landmark based on the analyzing of the slices of the scanned data.

6. The method according to claim 5, wherein the ground plane is defined by a plane passing through the center of each landmark of the at least three predetermined landmarks.

7. The method according to claim 6, further comprising a step of defining a triangular pyramid with a vertical apex being the center of the talar dome and a base being the ground plane.

8. The method according to claim 1, wherein the processor is configured to allow the user to rotate an image in the scanned data on the computer monitor to facilitate locating the three dimensional center point of each landmark.

9. The method according to claim 4, the method further comprising a step of receiving data representing a weight of the patient;
   wherein the step of determining the ankle offset lever arm involves steps of (i) determining an ankle offset point on the ground plane that is a first orthogonal projection from the ground plane to the center of the talar dome, (ii) determining a forefoot center point on the ground plane that is a midpoint between the center of the first metatarsal bone and the center of the fifth metatarsal bones, (iii) defining a line extending between the center of the greater tuberosity of the calcaneus to the forefoot center point, and (iv) wherein the ankle offset lever arm is a length of a second orthogonal projection on the ground plane from the line to the ankle offset point; and
   further comprising a step of determining a torque on an ankle bone of the patient by multiplying the weight of the patient times the ankle offset lever arm.

10. A method configured to be performed by a processor for determining an alignment measurement of foot and ankle bones of a patient while the patient is weight bearing, the method comprising the steps of:
    receiving scanned data representative of a three dimensional scanned image of the foot and ankle bones of the patient while the patient was applying weight on a foot;
    determining three dimensional coordinates in the scanned data of approximate centers of a first metatarsal bone, a fifth metatarsal bones and a greater tuberosity of a calcaneus;
    determining a ground plane defined by the centers of the first metatarsal bone, the fifth metatarsal bone and the greater tuberosity of the calcaneus;
    determining three dimensional coordinates in the scanned data of an approximate center of a talar dome based on a three dimensional shape of the talar dome, including a vertical and a horizontal location of the center of the talar dome relative to the ground plane;
    determining an ankle offset lever arm by (i) determining an ankle offset point on the ground plane that is an orthogonal projection from the ground plane to the center of the talar dome, (ii) determining a forefoot midpoint on the ground plane that is located at a midpoint between the centers of the first metatarsal bone and the fifth metatarsal bones, (iii) defining a line extending between the center of the greater tuberosity of the calcaneus and the forefoot midpoint, and (iv) wherein the ankle offset lever arm is a length of an orthogonal projection on the ground plane from the line to the ankle offset point;
    receiving data representing a weight of the patient, and determining a torque on the ankle bone of the patient by multiplying the weight of the patient times the ankle offset lever arm; and
    adjusting the torque by (i) calculating a length of the line between the forefoot midpoint and the center of the greater tuberosity of the calcaneus of the patient, (ii)

calculating a value by dividing the torque by the length of the line between the forefoot midpoint and the center of the greater tuberosity of the calcaneus of the patient, and (iii) multiplying the value that was calculated in (ii) by 100 to provide a percentage foot ankle offset; and outputting the percentage to a computer display.

* * * * *